(12) United States Patent
Miyahara

(10) Patent No.: US 7,083,605 B2
(45) Date of Patent: Aug. 1, 2006

(54) CONNECTOR SYSTEM FOR STERILE CONNECTION

(75) Inventor: Hideyasu Miyahara, Hiroshima (JP)

(73) Assignee: JMS Co., Ltd., Hirohima (JP)

( * ) Notice: Subject to any disclaimer, the term of this patent is extended or adjusted under 35 U.S.C. 154(b) by 577 days.

(21) Appl. No.: 10/353,112

(22) Filed: Jan. 27, 2003

(65) Prior Publication Data

US 2003/0144647 A1 Jul. 31, 2003

(30) Foreign Application Priority Data

Jan. 25, 2002 (JP) .................................. 2002-017075

(51) Int. Cl.
*A61M 5/32* (2006.01)

(52) U.S. Cl. ........................................ 604/415; 604/905

(58) Field of Classification Search ................ 604/905, 604/415, 284, 256, 244, 206, 167.01–167.06, 604/165.01–165.04, 91, 88, 86, 83; 285/331, 285/386

See application file for complete search history.

(56) References Cited

U.S. PATENT DOCUMENTS

| | | | |
|---|---|---|---|
| 3,986,508 A | * 10/1976 | Barrington | 604/411 |
| 4,511,359 A | * 4/1985 | Vaillancourt | 604/411 |
| 4,610,469 A | 9/1986 | Wolff-Mooij | |
| 4,878,516 A | 11/1989 | Mathieu | |
| 5,190,534 A | 3/1993 | Kendell | |
| 5,195,957 A | 3/1993 | Tollini | |
| 5,334,188 A | * 8/1994 | Inoue et al. | 604/539 |
| 5,423,775 A | * 6/1995 | Cannon | 604/533 |
| 5,792,120 A | 8/1998 | Menyhay | |

FOREIGN PATENT DOCUMENTS

| | | |
|---|---|---|
| JP | 6-312014 | 11/1994 |
| JP | 8-150216 | 6/1996 |
| WO | 94/08173 | 4/1994 |
| WO | 96/05882 | 2/1996 |
| WO | 97/35634 | 10/1997 |

* cited by examiner

*Primary Examiner*—Manuel Mendez
(74) *Attorney, Agent, or Firm*—Merchant & Gould P.C.

(57) ABSTRACT

A connector system for sterile connection includes a male type patient side connector having a tube connecting portion at a rear end portion thereof, a protective cap for the patient side connector, an inner cap held in the protective cap and including a ring-shaped portion that supports a disinfectant-impregnated member therein, and a female type circuit side connector including an outer cylinder and an inner cylinder fixed at one end of the outer cylinder, where the inner cylinder includes an internal end portion located inside the outer cylinder and an external end portion exposed outside the outer cylinder. When the protective cap is fitted with the patient side connector, the disinfectant-impregnated member contacts with the patient side connector. When the protective cap is removed therefrom, the inner cap becomes retained in the patient side connector. When such a patient side connector is connected with the circuit side connector, the internal end portion of the inner cylinder penetrates through the disinfectant-impregnated member and a septum. When the connection is released, the inner cap is detached from the patient side connector.

12 Claims, 9 Drawing Sheets

CONNECTOR SYSTEM FOR STERILE CONNECTION

BACKGROUND OF THE INVENTION

1. Field of the Invention

The present invention relates to a connector system for connecting a patient side transfer tube (extension tube) with a container of dialysis solution when a dialysis solution for peritoneal dialysis is exchanged. More particularly, the present invention relates to a connector system for sterile connection provided with a function of securely disinfecting a connecting portion with a simple operation when the connecting and detaching are repeated.

2. Related Background Art

Peritoneal dialysis is a medical treatment method in which a dialysis solution is stored in a patient's abdominal cavity by way of a peritoneal catheter that is implanted surgically in the patient's abdominal cavity beforehand, so that impurities accumulated in the body are filtered using capillary vessels in the peritoneum. The patient undertakes daily activities while a transfer tube (extension tube), which is used continuously for a half year, is connected to the end of the catheter. Then the patient himself connects a bag containing a dialysis solution with a front end of the transfer tube four times per day to exchange the dialysis solution in the abdominal cavity.

The most serious problem to be addressed for carrying out the peritoneal dialysis is bacteria in the air or attached to the skin mistakenly entering into the abdominal cavity during the operation of exchanging the dialysis solution as required four times per day. If bacteria enter into the abdominal cavity, these bacteria cause inflammation of the peritoneum to develop peritonitis. As a result, for treating the peritonitis, the catheter might be extracted in bad cases, which leads to a situation incapable of continuing the peritoneal dialysis. Furthermore, the peritonitis repeated for a long term degrades the function of a peritoneum, and as a result, sufficient efficiencies of the dialysis cannot be obtained, or the patient might suffer from sclerosing encapsulating peritonitis (SEP) that is intractable and leads to bad prognosis, including possible death.

Thus, in the peritoneal dialysis, it is important, when the dialysis solution is exchanged, to reduce the contamination by bacteria of a connector that connects a transfer tube and a container of dialysis solution. Conventionally, products for connecting tubes by melting with a heated copper plate or for disinfecting a connecting portion with ultraviolet rays are available commercially for preventing the contamination by bacteria. However, since these products necessarily require units dedicated to the products, a patient always has to carry the unit. Moreover, in the event of problems with the unit, serious problems might occur.

Meanwhile, in connection methods that do not use such units, a male and female screw type connector still is utilized. In these methods, since a channel for the dialysis solution necessarily becomes open in the connecting operation, it is virtually impossible to prevent the contamination by bacteria.

As for connecting members that do not require units and can prevent the contamination by bacteria, various structures have been examined until now. Examples of those ideas are a structure using a septum, which is pushed open to realize the fitting for connection, a structure where a lid member is opened and closed automatically when connectors are fitted, and a structure where fitting is realized by breaking a film covering a connecting portion.

However, all of those structures have problems in that their mechanism becomes complicated, their size becomes large and the required functions cannot be obtained sufficiently, and therefore none of them have been put into practical use.

SUMMARY OF THE INVENTION

Therefore, with the foregoing in mind, it is an object of the present invention to provide a connector system for sterile connection that enables connection with a simple operation for avoiding the contamination by bacteria, without substantially increasing the size of the conventional connectors.

The connector system for sterile connection of the present invention includes: a male type patient side connector including a tube connecting portion at a rear end portion thereof; a protective cap having a substantially cylindrical shape with a closed first end and being capable of connecting and disconnecting with/from a front end side of the patient side connector; an inner cap including a ring-shaped portion that supports a disinfectant-impregnated member therein, the inner cap being retained inside the protective cap in an initial state; and a female type circuit side connector having a double-cylinder structure in which an inner cylinder is fixed at one end portion of an outer cylinder, the inner cylinder including an internal end portion located inside the outer cylinder and an external end portion exposed outside the outer cylinder. The external end portion of the inner cylinder of the circuit side connector is capable of connecting with a front end of a circuit in a container of dialysis solution, and a channel for solution is connected by fitting the outer cylinder of the circuit side connector with the patient side connector. When the protective cap is fitted with the patient side connector, the inner cap assumes a state of being retained at the front end side of the patient side connector. When the protective cap is removed from the patient side connector, the inner cap is detached from the protective cap because of a retaining force at the front end side of the patient side connector. When the patient side connector with the inner cap retained at the front end thereof is connected with the circuit side connector, the internal end portion of the inner cylinder penetrates through the disinfectant-impregnated member in the inner cap, so that the channel is opened. When the connection between the patient side connector and the circuit side connector is released, the inner cap is retained inside the circuit side connector and is detached from the front end of the patient side connector.

With this configuration, the front end portion of the patient side connector continues to be disinfected by the disinfectant-impregnated member in the inner cap. In addition, when connecting with the circuit side connector, the inner cylinder of the circuit side connector also is disinfected by the disinfectant-impregnated member, so that bacteria do not intrude into the channel. Furthermore, every time the dialysis solution is exchanged, the inner cap is exchanged automatically into a new one, and therefore this system always is disinfected by a new disinfectant-impregnated member without a complicated procedure.

Preferably, the patient side connector includes a septum member at a front end portion thereof for protecting the channel, and when the patient side connector with the inner cap retained at the front end thereof is connected with the circuit side connector, the internal end portion of the inner cylinder penetrates through the disinfectant-impregnated member in the inner cap and the septum member of the patient side connector, so that the channel is opened.

Preferably, the inner cap includes a plurality of engaging legs extending from an outer edge portion of the ring-shaped portion in a direction along an axis of the ring. An engaging convexity is formed at a front end of each of the engaging legs so as to protrude inward. Engaging concavities are formed on an outer surface of the front end portion of the patient side connector so as to allow engagement with the engaging convexities formed at the engaging legs of the inner cap. An inner cap retaining portion is formed on an inner wall inside the protective cap, where a retaining force exerted by the engagement between the engaging convexity of the inner cap and the engaging concavity of the patient side connector is larger than a force exerted by the inner cap retaining portion of the protective cap to retain the inner cap. When the protective cap with the inner cap retained therein is fitted with the patient side connector, the engaging convexities of the inner cap engage with the engaging concavities of the patient side connector, and when the protective cap is removed from the patient side connector, the retaining of the inner cap by the inner cap retaining portion of the protective cap is released due to the retaining of the inner cap at the engaging concavities of the patient side connector, so that the inner cap is detached from the protective cap while being fitted with the front end of the patient side connector.

In the above configuration, preferably, on the outer surface of the patient side connector, a circumferential step portion extending in a circumferential direction is formed so that a diameter at the front end side of the patient side connector is smaller than that at a base end side, and a guide groove is formed so as to extend from the circumferential step portion toward the base end. The guide groove includes an inclined portion that is inclined with respect to an axis of the patient side connector. On the inner wall close to an opening end portion of the protective cap, a guide protrusion is formed, and on the inner wall and extending toward the closed end side of the protective cap, a rotation blocking step portion is formed, the rotation blocking step portion being capable of contacting with the engaging legs of the inner cap so as to block a rotational action of the inner cap. When the patient side connector is inserted into an opening of the protective cap with the guide protrusion of the protective cap facing the guide groove of the patient side connector, and then the protective cap and the patient side connector are rotated while being urged axially toward each other, the guide protrusion slides along the guide groove, so that the patient side connector is pulled into an inside of the protective cap by a driving force resulting from a screw action by the inclined portion of the guide groove, and the engaging convexities of the inner cap, whose rotation is blocked by the rotation blocking step portion, engage with the engaging concavities of the patient side connector.

In the above configuration, preferably, the patient side connector includes a blocking wall at the front end portion thereof, which is capable of contacting with a side face portion of the engaging leg of the inner cap when the inner cap is fitted thereto. The outer cylinder of the circuit side connector includes: a guide protrusion formed on an inner wall close to an open end portion thereof, the guide protrusion being formed to correspond to the guide protrusion of the protective cap; a guide step portion including an inclined portion that is inclined with respect to an axis of the circuit side connector; and an inner cap retaining portion formed at an inside of the connector and being capable of retaining the inner cap. When the patient side connector with the inner cap retained therein is inserted into the opening of the circuit side connector with the guide protrusion of the outer cylinder facing the guide groove of the patient side connector, and then the circuit side connector and the patient side connector are rotated while being urged axially toward each other, the guide protrusion slides along the guide groove, so that the patient side connector is pulled into the inside of the circuit side connector by a driving force resulting from a screw action by the inclined portion of the guide groove. At the same time the front ends of the engaging legs of the inner cap slide along the inclined portion of the guide step portion of the circuit side connector while rotation of the inner cap is blocked by the blocking wall of the patient side connector, so that a force in the axis direction acts on the inner cap so as to separate the inner cap from the patient side connector, resulting in the release of the engagement between the inner cap and the patient side connector, and the inner cap assumes a state of being retained by the inner cap retaining portion of the outer cylinder. The two guide protrusions (i.e., of the patient side connector and of the protective cap) are formed so that they will act in the same manner and perform a similar function.

In the above configuration, preferably, the inner cap retaining portion of the circuit side connector is configured with a horizontal step portion provided at the innermost of the guide step portion. When the front ends of the engaging legs of the inner cap contact with the horizontal step portion, the inner cap is prevented from moving in the axis direction toward the opening of the outer cylinder so as to be retained in the circuit side connector.

In the above configuration, preferably, the inner cap retaining portion of the circuit side connector is configured by setting the dimensions of constituting elements so that at least portions of the inner wall of the inside of the outer cylinder contact with an outer circumferential surface of the ring-shaped portion of the inner cap or so that at least portions of the outer wall of the internal end portion of the inner cylinder contact with an inner circumferential surface of the ring-shaped portion of the inner cap, whereby the inner cap is retained by the thus generated frictional force.

In the above configuration, preferably, the inner cap retaining portion of the protective cap is configured with a convex stripe formed on the inner wall of the inside of the protective cap, and the convex stripe contacts with an outer circumferential surface of the ring-shaped portion of the inner cap, so that the inner cap is retained by the thus generated frictional force.

In the above configuration, preferably, on the outer surface of the front end portion of the patient side connector, a convex stripe is formed so as to extend in the axis direction to a portion close to a joining portion between the guide groove and the circumferential direction step portion, and when the protective cap or the circuit side connector is combined with the patient side connector, the convex stripe guides the guide protrusion of each of the protective cap and the circuit side connector to the guide groove.

The circuit side connector used in the above connector system for sterile connection includes a double-cylinder structure in which an inner cylinder is fixed at one end portion of an outer cylinder. The inner cylinder includes an internal end portion located inside the outer cylinder and an external end portion exposed outside the outer cylinder.

The protective cap assembled member used in the above connector system for sterile connection includes: the protective cap having a substantially cylindrical shape whose one end is closed; and the inner cap retained at an inside of the protective cap and including a ring-shaped portion with a disinfectant-impregnated member supported therein. On an inner wall of the inside of the protective cap, an inner cap retaining portion for retaining the inner cap is formed. The inner cap includes a plurality of engaging legs extending from an outer edge portion of the ring-shaped portion in a direction along an axis of the ring, and an engaging convexity is formed at each of the engaging legs so as to protrude inward. The inner cap is retained by the inner cap retaining portion so that the front ends of the engaging legs are directed toward an opening of the protective cap.

The patient side connector used in the above connector system for sterile connection includes engaging concavities formed on an outer surface of the front end portion thereof so as to allow engagement with the engaging convexities formed at the engaging legs of the inner cap.

DETAILED DESCRIPTION OF THE INVENTION

Figure 1A:
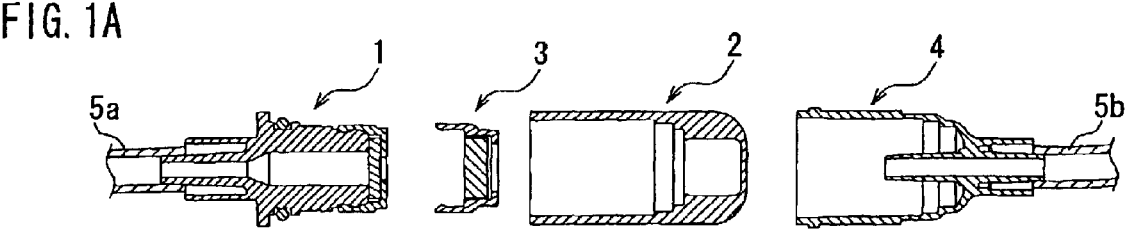
FIGS. 1A to 1G are front cross-sectional views showing each element constituting a connector system for sterile connection according to one embodiment of the present invention and their operation.

The following describes a configuration of a connector system for sterile connection according to one embodiment of the present invention, with reference to FIGS. 1 to 7. As indicated by an exploded view of FIG. 1A, this connector system for sterile connection includes a patient side connector 1, a protective cap 2, an inner cap 3 and a circuit side connector 4.

The patient side connector 1 is connected to a front end of an extension tube 5a that leads to a peritoneal catheter implanted in a patient's abdominal cavity. The circuit side connector 4 is connected to an extension tube 5b as a front end of a circuit in a container of dialysis solution, such as a twin bag, BF and APD. The inner cap 3 initially is supplied in a state of being supported in the protective cap 2, as shown on the right side of FIG. 1B. The inner cap 3 is equipped with a disinfectant-impregnated member, such as a disinfecting sponge impregnated with a disinfectant, which will be described later. The outline of a function of each element constituting this connector system for sterile connection will be described below, with reference to FIGS. 1B to 1G.

Figure 1B:
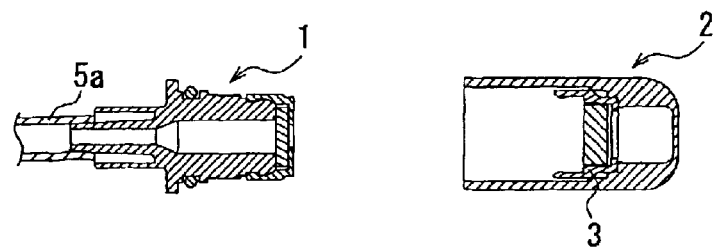
Figure 1C:
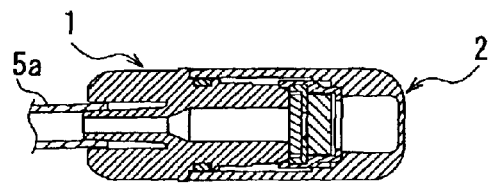

The patient side connector 1 is connected to the front end of the extension tube 5a, which is used during a long term use for a half year. The protective cap 2 is fitted with the patient side connector 1 always during daily activities for protecting the front end of the connector. For this purpose, as shown in FIG. 1B, the protective cap 2 that supports a newly-prepared inner cap 3 therein is opposed to the patient side connector 1, and they are fitted with each other as shown in FIG. 1C. In this state, the disinfectant-impregnated member provided in the inner cap 3 contacts with an end face of the patient side connector 1 so as to perform a disinfecting function.

Figure 1D:
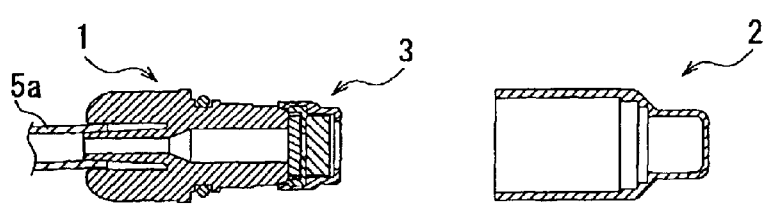
Figure 1E:
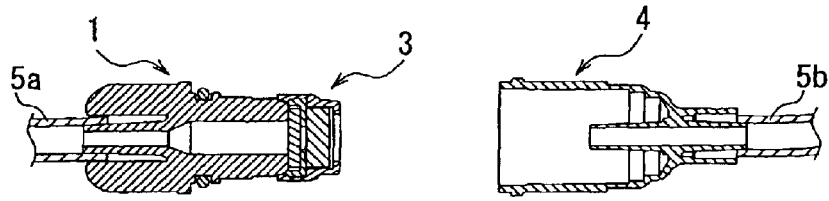
Figure 1F:
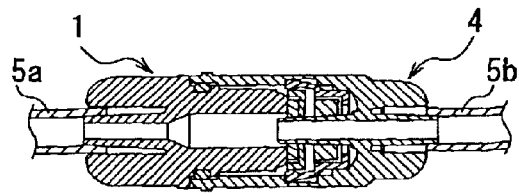
Figure 1G:
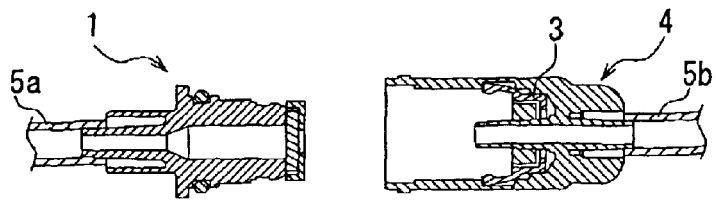

When a dialysis solution is exchanged, firstly, the protective cap 2 is removed from the patient side connector 1. In this removal operation, the inner cap 3 is transferred from the protective cap 2 to the patient side connector 1 as shown in FIG. 1D. In this exchanging operation of the dialysis solution, as shown in FIG. 1E, the circuit side connector 4 is opposed to the patient side connector 1 and, as shown in FIG. 1F, is connected with the patient side connector 1, thus forming a channel leading from the twin bag or the like to the patient's abdominal cavity. When the dialysis solution has been exchanged, as shown in FIG. 1G, the connection between the patient side connector 1 and the circuit side connector 4 is released. Then, the inner cap 3 finally is transferred to the circuit side connector 4 in accordance with the operation that will be described later, and is discarded together with the circuit side connector 4.

Figure 2:
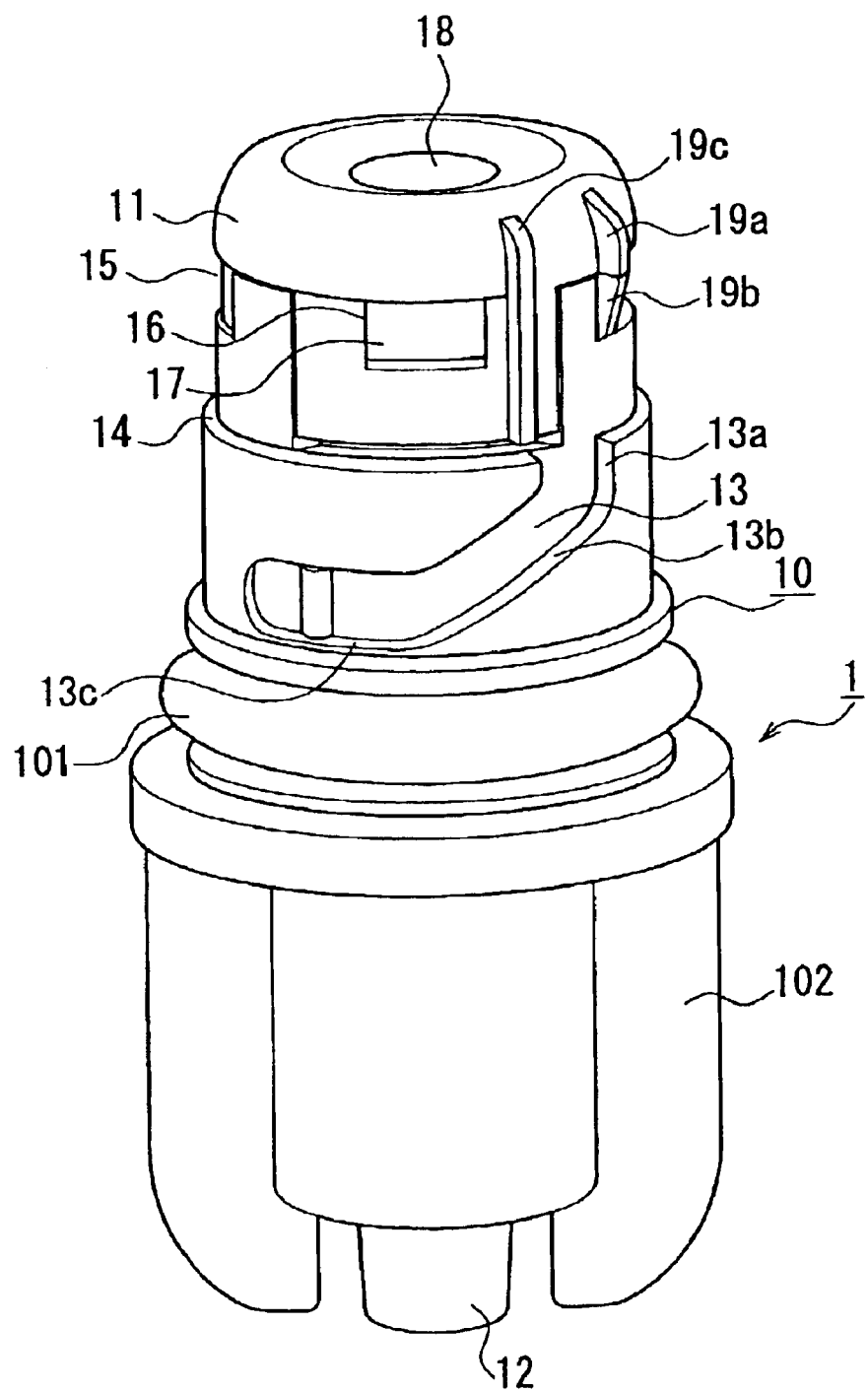
FIG. 2 is a perspective view showing a patient side connector constituting the connector system for sterile connection according to the embodiment of the present invention.
Figure 3:
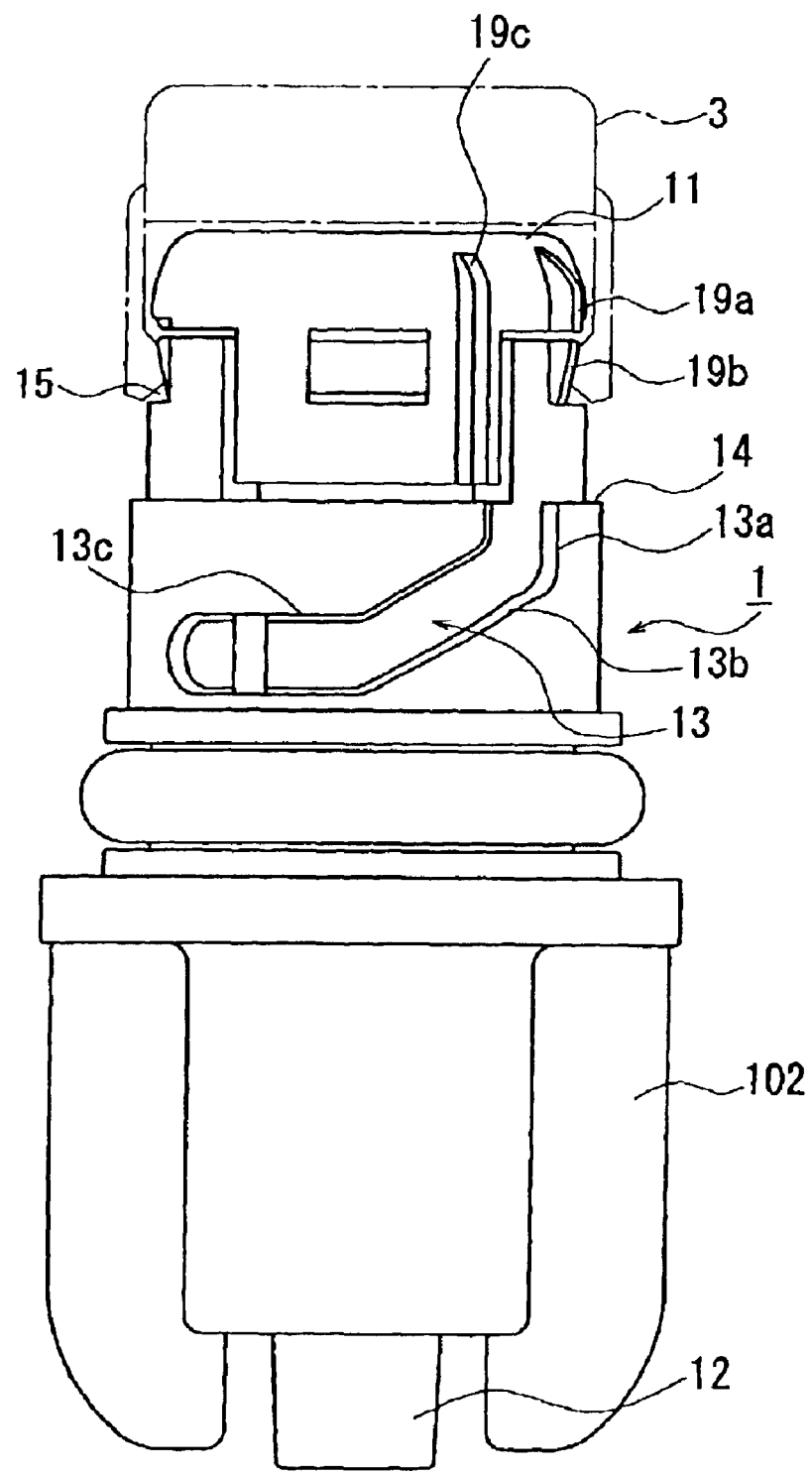
FIG. 3 is a front view showing the patient side connector.

Each of the above constituting elements will be described below in detail. The patient side connector 1, as shown in FIGS. 2 and 3, includes a substantially cylindrical-shaped main body 10 made of resin, a septum supporting member 11 made of resin, which is fitted to a front end of the main body 10, and an O ring 101. At a base end (rear end) of the main body 10, a tube-shaped tube connecting portion 12 is formed for the connection with the extension tube (not illustrated). On either side of the tube connecting portion 12, a knob 102 is provided for supporting firmly when the patient side connector 1 is rotated.

Inside the main body 10, a channel is formed so as to penetrate from its front end to the tube connecting portion 12. On an outer surface of the central portion of the main body 10, a guide groove 13 is formed. A pair of the guide grooves 13 is provided symmetrically with respect to the axis of the main body 10, and one of the guide grooves 13 is located on the reverse side of FIG. 2. The pair of guide grooves 13 is not necessarily required, and only one guide groove may function sufficiently. The guide groove 13 includes an axis direction portion 13a extending in the axis direction of the main body 10, an inclined portion 13b that is inclined and a circumferential portion 13c extending along the circumferential direction. The axis direction portion 13a on the front end side ends with a step portion 14 formed on the outer surface of the main body 10. The step portion 14 is formed in the circumferential direction so that an outer diameter of the main body 10 at the front end side becomes smaller than at the base end side.

On the outer surface of a front end portion of the main body 10, an engaging concavity 15 is formed. The engaging concavity 15 is provided for supporting the inner cap 3 as indicated by alternate long and short dash lines in FIG. 3. This structure will be further described later. The septum supporting member 11 has a fitting hole 16, and the septum supporting member 11 is fixed to the main body 10 by the fitting between this fitting hole 16 and a protrusion 17 provided on the main body 10. At a central portion of the septum supporting member 11, a septum member such as a rubber septum (member with a slit) 18 is provided so as to protect the channel and ensure liquid-tightness. On a side surface of the septum supporting member 11 and a side surface of the front end portion of the main body 10, blocking walls 19a and 19b respectively are formed. A convex stripe 19c is provided for guiding a guide protrusion 21, etc., formed on an inner wall of the protective cap 2, which will be described later, to the axis direction portion 13a of the guide groove 13. Note here that the septum 18 is effective for ensuring liquid-tightness in the connecting state with the circuit side connector 4, but this element is not essential. Therefore, the liquid-tight seal may be ensured by other methods. In such cases, since the septum supporting member 11 is not used, the blocking walls 19a, 19b and the convex stripe 19c are formed directly on the main body 10.

Figure 4:
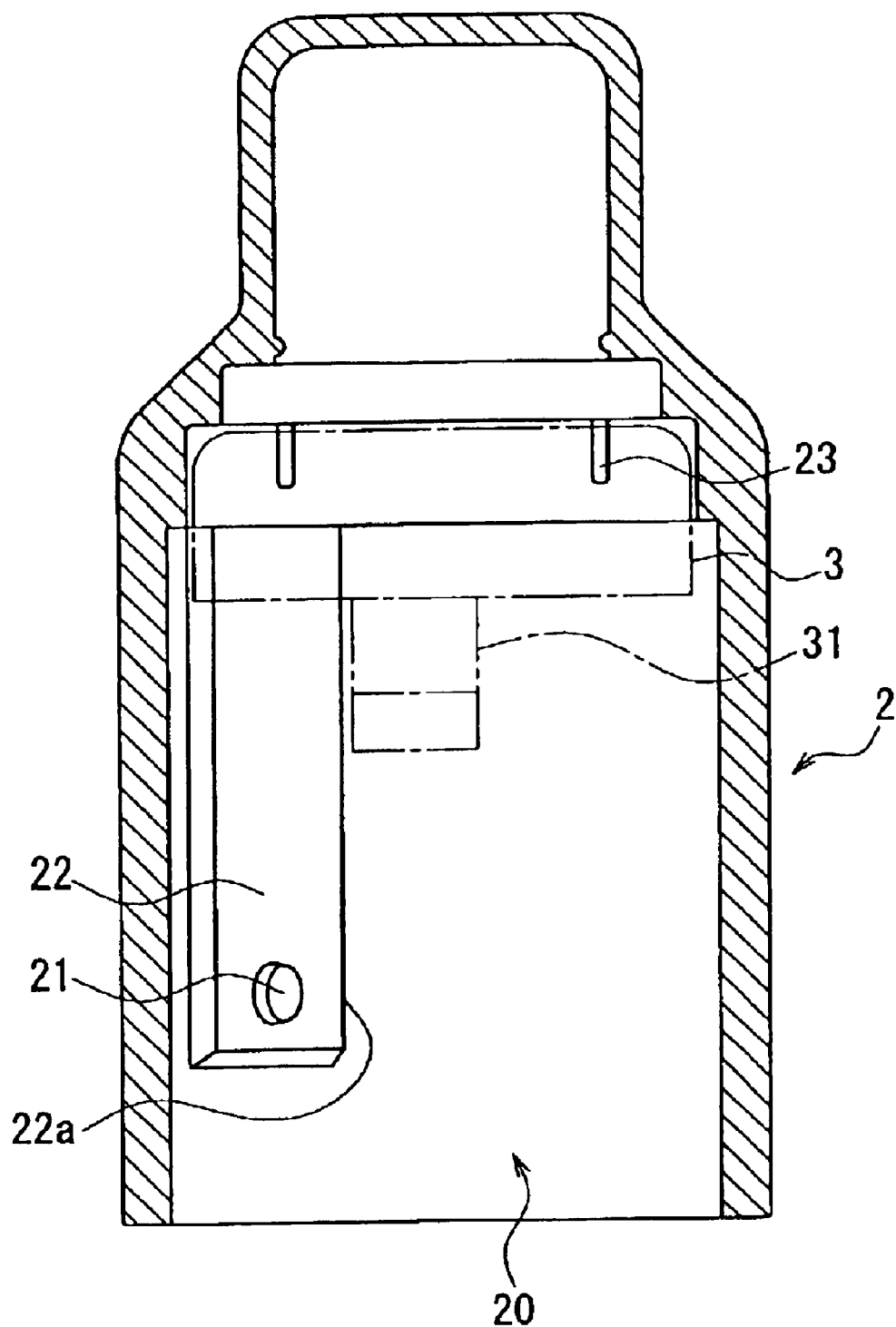
FIG. 4 is a cross-sectional view showing a protective cap constituting the connector system for sterile connection according to the embodiment of the present invention.

The protective cap 2 may be made of resin and, as shown in FIG. 4, has a hollow structure with a substantially cylindrical shape whose front end is closed. On an inner wall close to an opening 20 of the protective cap 2, a guide protrusion 21 is formed and located on a projected portion 22 that projects like a rectangular island. A rotation-blocking step portion 22a is formed with an edge of the projected portion 22 along the axis direction. Although a pair of the guide protrusions 21 and a pair of the projected portions 22 are provided symmetrically, only one of them is illustrated in this drawing. On an inner circumferential surface of the closed end of the protective cap 2, a convex stripe 23 is formed. At this portion, the inner cap 3 is placed as indicated by the alternate long and short dash lines, and the inner cap 3 is supported by frictional engagement between the outer circumferential surface of a ring-shaped portion 30 (FIG. 5) of the inner cap 3 and the convex stripe 23. By inserting the patient side connector 1 into the opening 20, the protective cap 2 is fitted with the front end of the patient side connector 1. In this operation, the guide protrusion 21 engages with the guide groove 13 in the patient side connector 1, and a mutual positional relationship between the protective cap 2 and the patient side connector 1 is guided by the engagement, so that the fitting is conducted. This operation will be described later.

Figure 5A:
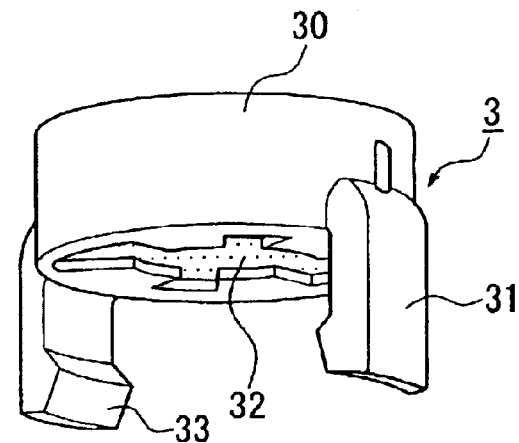
FIG. 5A is a perspective view showing an inner cap constituting the connector system for sterile connection.
Figure 5B:
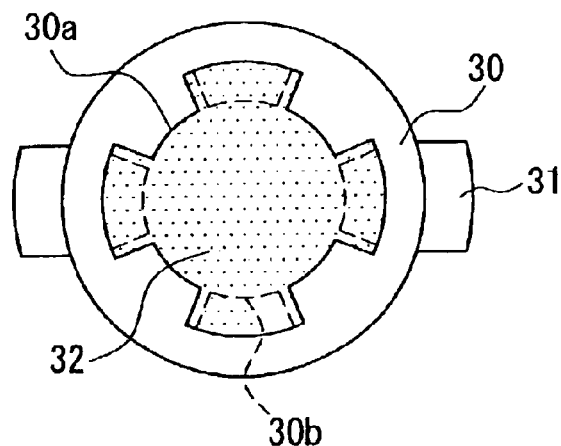
FIG. 5B is a plan view of the same and FIG. 5C is a cross-sectional view of the same.
Figure 5C:
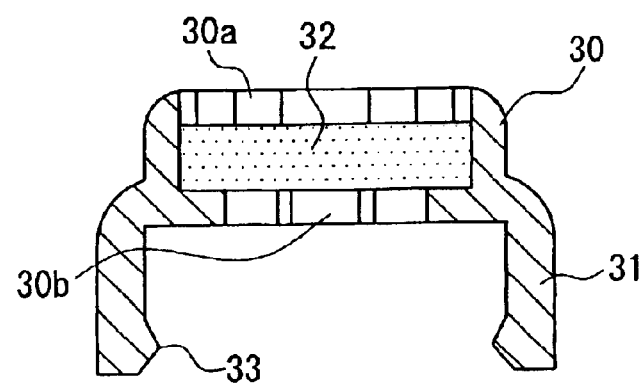

The inner cap 3 may be made of resin and, as shown in FIGS. 5A–C, includes the ring-shaped portion 30 and two engaging legs 31. Inside the ring-shaped portion 30, a disinfecting sponge 32 is installed. Inside the ring-shaped portion 30, inward protrusions 30a and 30b are formed at plural portions. The inward protrusions 30a are arranged at an upper end in the axis direction, whereas the inward protrusions 30b are arranged at a lower end in the axis direction. Between the inward protrusions 30a and 30b, the disinfecting sponge 32 is supported. A straight-line or cross-shaped slit (not illustrated) may be provided in the disinfecting sponge 32 so that an internal end portion 41b of the circuit side connector 4, which will be described later, can penetrate therethrough, and the disinfecting sponge 32 is impregnated with a disinfectant such as Isodine. The engaging legs 31 protrude outward in the radial direction from the outer circumferential surface of the ring-shaped portion 30. At a front end of each of the engaging legs 31, an engaging convexity 33 is formed so as to protrude inward. As previously described, the inner cap 3 initially is held in the protective cap 2 as shown in FIG. 4. When the protective cap 2 is fitted with the patient side connector 1, the engaging convexity 33 of the inner cap 3 engages with the engaging convexity 15 of the patient side connector 1. Thereby, the inner cap 3 is retained on the septum supporting member 11.

As stated above, the inner cap 3 is retained in the protective cap 2 by the friction engagement with the convex stripe 23 in the protective cap 2. Also, the inner cap 3 is retained on the patient side connector 1 by the engagement between the engaging concavity 15 of the patient side connector 1 and the engaging convexity 33 of the inner cap 3. These modes for retaining the inner cap 3 are set so that the retaining force by the friction engagement in the protective cap 2 becomes smaller than the retaining force on the patient side connector 1.

Figure 6:
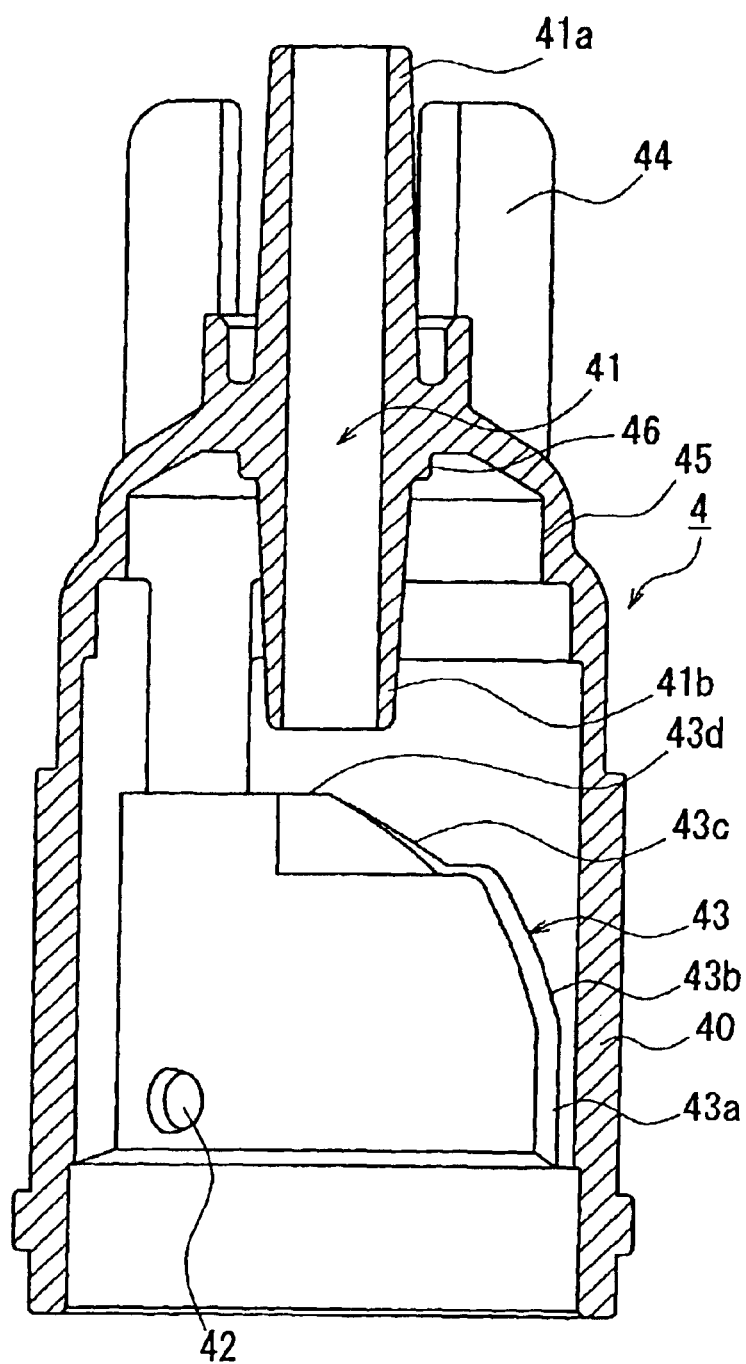
FIG. 6 is a cross-sectional view showing a circuit side connector constituting the connector system for sterile connection.
Figure 7:
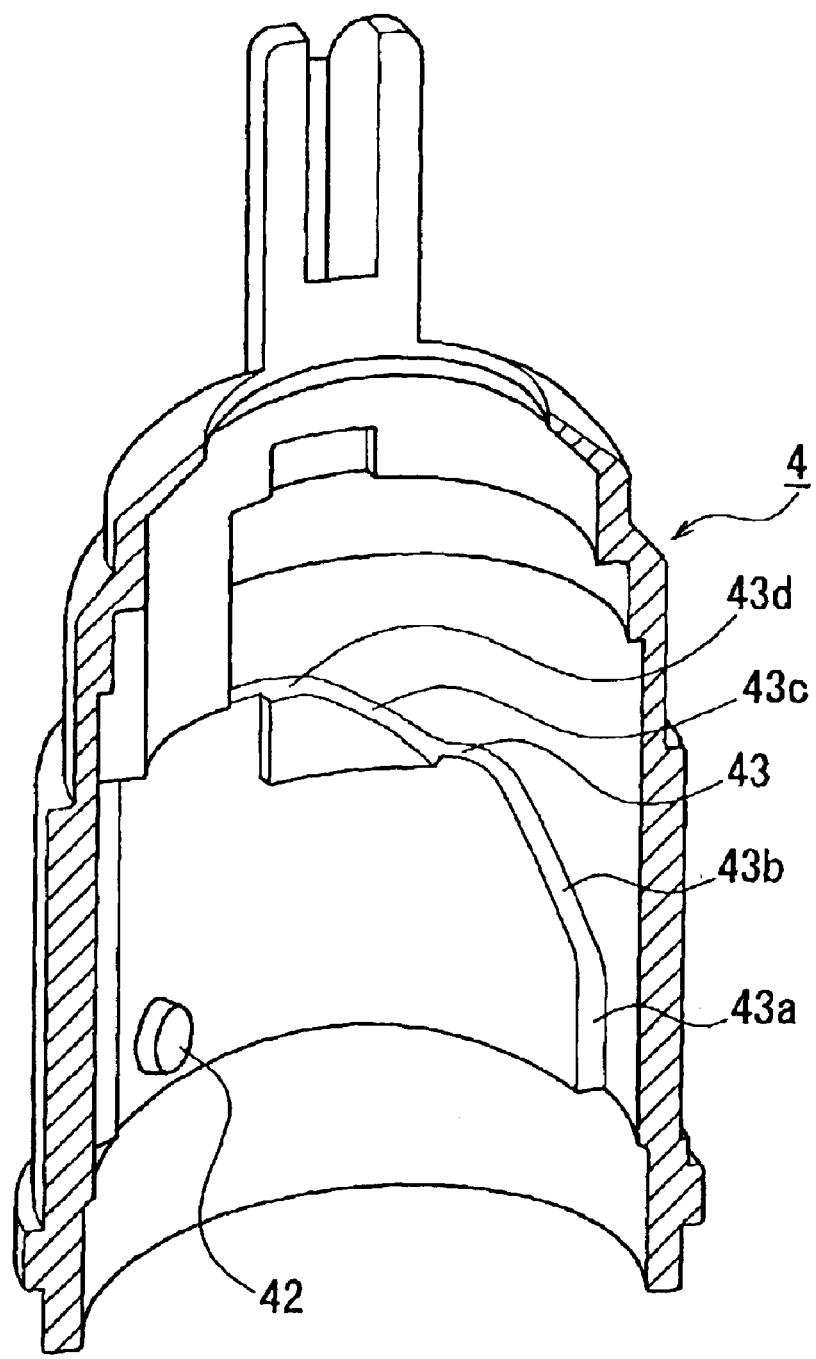
FIG. 7 is a cross-sectional view of the circuit side connector in perspective.

FIGS. 6 and 7 show the structure of the circuit side connector 4. As shown in FIG. 6, the circuit side connector 4 has a double-cylinder structure made of resin, in which an inner cylinder 41 is fixed at one end portion of an outer cylinder 40. Note here that FIG. 7 omits the inner cylinder 41. The outer cylinder 40 is open at a lower end in this drawing to constitute a front end portion of the circuit side connector 4. The inner cylinder 41 includes an external end portion 41a exposed outside the outer cylinder 40 and the internal end portion 41b located inside the outer cylinder 40. The external end portion 41a is to be connected with a tube as the front end of the circuit in the container of dialysis solution. When connecting the circuit side connector 4 and the patient side connector 1, the internal end portion 41b pushes and expands the slit in the disinfecting sponge 32 in the inner cap 3 fitted with the patient side connector 1 and the slit in the rubber septum 18 supported by the septum supporting member 11 so as to penetrate through the patient side connector 1, whereby the channel is opened.

On an inner wall of the opening end portion (the lower end portion in the drawings) of the outer cylinder 40, a guide protrusion 42 is formed in the same manner as the guide protrusion 21 formed in the protective cap 2. Also on the inner wall of the outer cylinder 40, a guide step portion 43 is formed so as to extend from the lower end portion to the central portion. The guide step portion 43 includes, as clearly illustrated in FIG. 7, clearance step portions 43a and 43b, an inclined step portion 43c and a horizontal step portion 43d, whose shapes and arrangement are set suitably for their functions that will be described later.

The horizontal step portion 43d functions as means for retaining the inner cap 3 at an inside (an upper end portion in these drawings) of the outer cylinder 40. That is, when the inner cap 3 is pushed into the inside of the outer cylinder 40 and the front ends of the engaging legs 31 contact with the horizontal step portion 43d, the inner cap 3 is retained there. The operation for the same will be described later. Alternatively, another retaining means may be configured so that at least portions of an inner wall 45 of the inside of the outer cylinder 40 contact with an outer circumferential surface of the ring-shaped portion 30 of the inner cap 3, whereby the inner cap 3 is retained by the thus generated frictional force. For such function, inward protrusions formed at plural portions on the inner wall 45 of the inside are effective. Alternatively, a plurality of outward protrusions 46 may be provided on an outer wall of the internal end portion 41b of the inner cylinder 41 so as to contact with an inner circumferential surface of the ring-shaped portion 30 of the inner cap 3, whereby the inner cap 3 is retained by the thus generated frictional force.

In a state before use, a breakable film (not illustrated) is provided at the front end portion of the outer cylinder 40 of the circuit side connector 4 for protecting the inner cylinder and the channel in the circuit side connector 4 until immediately before use. At a rear end portion of the outer cylinder 40, operating knobs 44 are formed along the external end portion 41a of the inner cylinder 41.

Next, the operation of the connector system for sterile connection having the above configuration will be described below. Note here that the specification and claims may refer to rotation or other movement of a particular element for a simpler description, but that it should be understood that this is defining relative movement between the elements, and that either one of the elements can be moved and either one fixed, or both moved, to accomplish the relative movement.

Figure 8A:
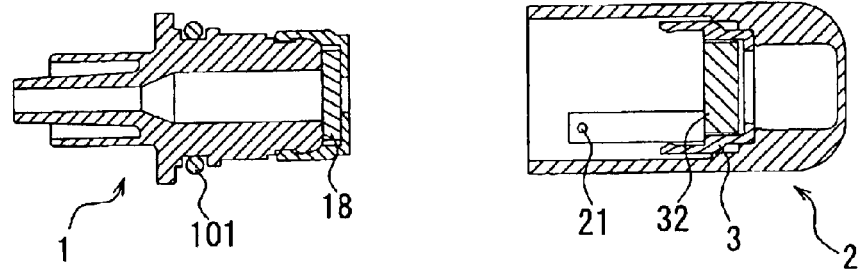
FIGS. 8A to 8E are cross-sectional views illustrating the operation of fitting the protective cap with the patient side connector, which constitute the connector system for sterile connection according to the embodiment of the present invention.

Firstly, the operation for fitting the protective cap 2 with the patient side connector 1 will be described, with reference to FIG. 8. FIGS. 8A to 8D illustrate each state during an operation in which the patient side connector 1 is rotated while the protective cap 2 is fixed. The protective cap 2 is illustrated in a state rotated around the axis by 90° from the state shown in FIG. 4. The patient side connector 1 of FIG. 8A is in a state rotated around the axis by 90° clockwise from the angle shown in FIG. 3. From this state, by rotating the patient side connector 1 clockwise by 90° when viewed from the left side, the state of FIG. 8D is obtained. FIG. 8E shows a state where the protective cap 2 is rotated by 90° from the state shown in FIG. 8D.

Figure 8B:
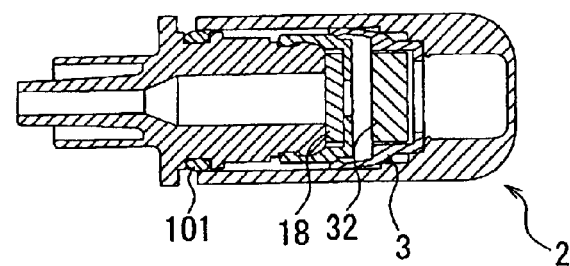
Figure 8C:
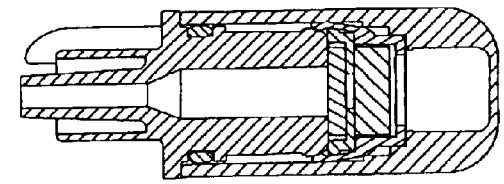
Figure 8D:
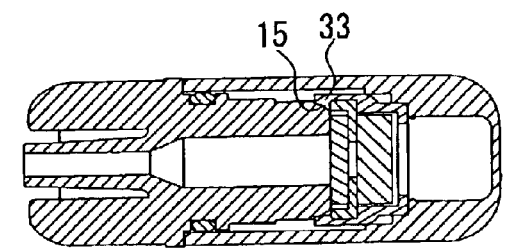
Figure 8E:
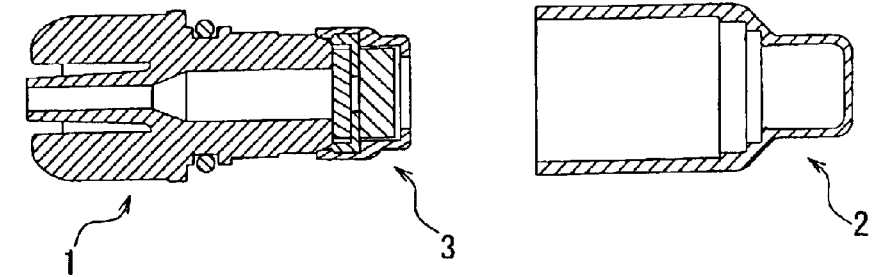

To begin with, as shown in FIG. 8A, a newly-prepared protective cap 3 that retains an inner cap 3 therein is opposed to the patient side connector 1, and then as shown in FIG. 8B, the patient side connector 1 is inserted into the protective cap 2. During this operation, the guide protrusion 21 formed on the inner wall of the protective cap 2 contacts with the step portion 14 on the outer surface of the patient side connector 1 (See FIGS. 2 to 4). By rotating the protective cap 2 relative to the patient side connector 1, the guide protrusion 21 contacts with the convex stripe 19c, so that the guide protrusion 21 faces a portion of the axis direction portion 13a of the guide groove 13. With this operation, the patient side connector 1 becomes capable of being inserted further into the protective cap 2. From this position, the patient side connector 1 is pushed inside, and as shown in FIG. 8C, the patient side connector 1 further is rotated clockwise. That is, the operation is conducted so that the guide protrusion 21 slides along the inclined portion 13b of the guide groove 13. With this operation, by a screw action through the engagement between the guide protrusion 21 and the guide groove 13, the patient side connector 1 is pulled into the innermost of the protective cap 2. By rotating further, the guide protrusion 21 enters into the circumferential portion 13c. As a result, by the engagement of the guide protrusion 21 and the circumferential portion 13c, the protective cap 2 and the patient side connector 1 are combined so as not to separate from each other in the axis direction.

During this operation, the front end portion of the patient side connector 1 pushes the engaging legs 31 of the inner cap 3 outward. The inner cap 3 is prevented from rotating because the engaging legs 31 are blocked by the rotation-blocking step portion 22a of the protective cap 2, so that the engaging convexities 33 of the engaging legs 31 slide on the outer circumferential surface of the front end portion of the patient side connector 1. Finally, as shown in FIG. 8D, the engaging convexities 33 engage with the engaging concavities 15 of the patient side connector 1. In this state, the disinfecting sponge 32 in the inner cap 3 continues to disinfect the septum 18 at the front end of the patient side connector 1 while a patient engages in daily activities. In addition, since the inner circumferential surface of the open end of the protective cap 2 contacts with the O ring 101, the liquid-tightness inside the protective cap 2 can be maintained and the front end of the patient side connector 1 can be protected from the air.

Next, the operation for removing the protective cap 2 from the state shown in FIG. 8D to exchange the dialysis solution will be described below. By rotating the protective cap 2 opposite to the direction for the fitting, the inner cap 3 rotates with respect to the protective cap 2 together with the patient side connector 1 by the retaining due to the engagement between the engaging convexities 33 and the engaging concavities 15 of the patient side connector 1. With this rotation, the guide protrusion 21 of the protective cap 2 slides along the guide groove 13 and reaches a junction between the axis direction portion 13a and the step portion 14. From this state, by separating the patient side connector 1 from the protective cap 2 in the axis direction, the patient side connector 1 is removed from the protective cap 2 while the inner cap 3 is fitted with the front end of the patient side connector 1 so as to assume a state shown in FIG. 8E.

Figure 9A:
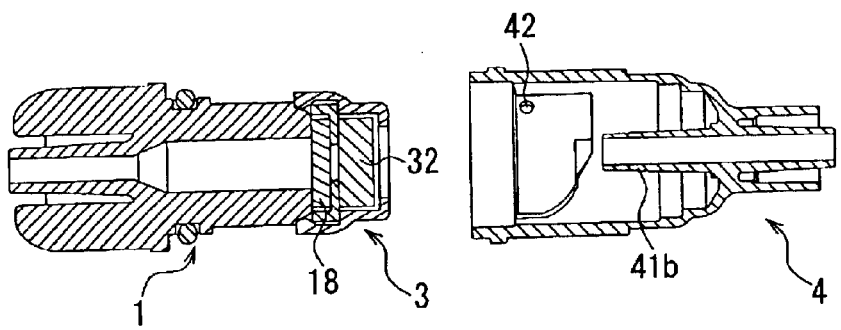
FIGS. 9A to 9E are cross-sectional views illustrating the operation of connecting the patient side connector and the circuit side connector according to the same.
Figure 9B:
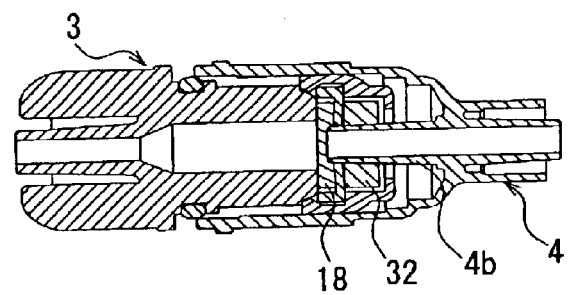
Figure 9C:
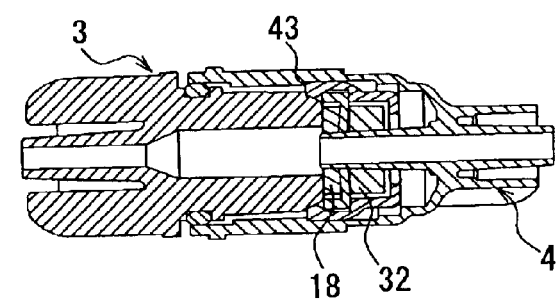
Figure 9D:
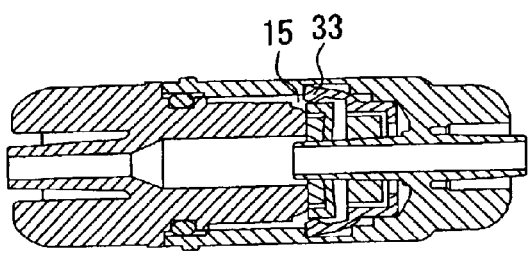
Figure 9E:
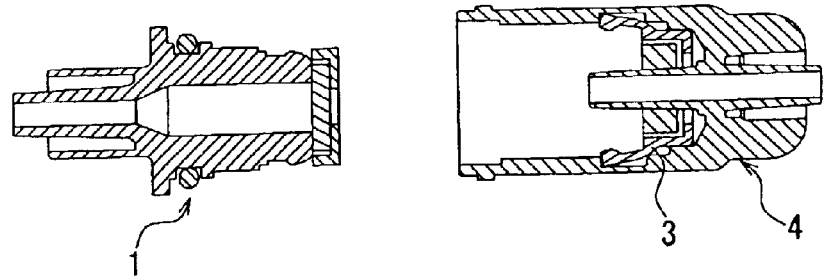

Next, the operation for connecting the patient side connector 1 and the circuit side connector 4 will be described below, with reference to FIG. 9. FIGS. 9A to 9D illustrate each state during an operation in which the circuit side connector 4 is rotated while the patient side connector 1 is fixed. The patient side connector 1 is illustrated in the same angle as in FIG. 8E. The circuit side connector 4 of FIG. 9A is illustrated in the angle of FIG. 6. By rotating the circuit side connector 4 by 90° counterclockwise when viewed from the patient side connector 1 side, the state of FIG. 9D is obtained. FIG. 9E illustrates a state where the patient side connector 1 is rotated by 90° from the state shown in FIG. 9D.

Firstly, as shown in FIG. 9A, the patient side connector 1 and the circuit side connector 4 are opposed to each other. In this state, the inner cap 3 is fitted with the front end of the patient side connector 1. Next, as shown in FIG. 9B, the patient side connector 1 is inserted into the circuit side connector 4. In this operation, the guide protrusion 42 formed on the inner wall of the circuit side connector 4 contacts with the step portion 14 on the outer surface of the patient side connector 1. The circuit side connector 4 is rotated properly so that the guide protrusion 42 faces a position on a junction between the axis direction portion 13a of the guide groove 13 and the step portion 14, whereby the patient side connector 1 becomes capable of being inserted further into the circuit side connector 4. In this state, the engaging legs 31 of the inner cap 3 are located on the right side of the clearance step portions 43a and 43b shown in FIG. 7. Therefore, when the patient side connector 1 further is inserted, the engaging legs 31 are located to escape from the guide step portion 43.

In order to insert the patient side connector 1 into an inside, the patient side connector 1 is pushed inward from this position, while rotating the circuit side connector 4 clockwise. With this operation, the guide protrusion 42 slides along the inclined portion 13b of the guide groove 13. According to a screw action generated between the guide protrusion 42 and the guide groove 13, the patient side connector 1 reaches the inside of the circuit side connector 4 as shown in FIG. 9C. By rotating further, the guide protrusion 42 enters into the circumferential portion 13c.

During the process of the guide protrusion 42 sliding along the circumferential portion 13c, the front ends of the engaging legs 31 of the inner cap 3 that is fitted with the front end of the patient side connector 1 contact with the inclined step portion 43c. By the rotational force exerted through the contact between the side surfaces of the engaging legs 31 and the blocking walls 19a and 19b of the patient side connector 1, the front ends of the engaging legs 31 slide along the inclined step portion 43c. Thereby, the inner cap 3 receives a force in the axis direction toward an inside of the circuit side connector 4 from the inclined step portion 43c. As a result, as shown in FIG. 9D, the engagement between the engaging convexities 33 formed at the front ends of the engaging legs 31 of the inner cap 3 and the engaging concavities 15 of the patient side connector 1 is released. Finally, the front ends of the engaging legs 31 reach the horizontal step portion 43d, and the inner cap 3 is retained in the circuit side connector 4 in this state. That is to say, when the patient side connector 1 is rotated counterclockwise to release the connection between the patient side connector 1 and the circuit side connector 4, the inner cap 3 is not rotated because the engagement between the engaging concavities 15 and the engaging convexities 33 has been released. Moreover, since the front ends of the engaging legs 31 and the horizontal step portion 43d are engaged, the inner cap 3 does not move in the axis direction so as to be detached from the circuit side connector 4.

In addition, when the circuit side connector 4 and the patient side connector 1 are connected as described above, the internal end portion 41b of the inner cylinder 41 of the circuit side connector 4 pushes and expands the slit in the disinfecting sponge 32 in the inner cap 3 fitted with the front end of the patient side connector 1 and the slit in the rubber septum 18 supported by the septum supporting member 11 so as to penetrate through the patient side connector 1, whereby the channel is opened. In this process, the channel is formed while the inner cylinder 41 is disinfected by the disinfecting sponge 32.

After the draining and filling of the peritoneal dialysis solution have been completed, when the circuit side connector 4 is removed, the patient side connector 1 is rotated counterclockwise. With this operation, the engagement between the guide protrusion 42 and the guide groove 13 is released, and therefore the connection between both connectors is released. In this operation, as described above, the inner cap 3 is left in the circuit side connector 4 (FIG. 9E).

After that, by fitting a newly-prepared protective cap 2, a new inner cap 3 is fitted with the front end of the patient side connector 1, whereby as stated above the front end portion of the patient side connector 1 continues to be disinfected until the next exchanging operation of the dialysis solution.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A connector system for sterile connection comprising:
   a male type patient side connector including a tube connecting portion at a rear end portion thereof;
   a protective cap having a substantially cylindrical shape with a closed first end and being capable of connecting and disconnecting with/from a front end side of the patient side connector;
   an inner cap including a ring-shaped portion that supports a disinfectant-impregnated member therein, the inner cap being retained inside the protective cap in an initial state; and
   a female type circuit side connector having a double-cylinder structure in which an inner cylinder is fixed at one end portion of an outer cylinder, the inner cylinder including an internal end portion located inside the outer cylinder and an external end portion exposed outside the outer cylinder,
   wherein the external end portion of the inner cylinder of the circuit side connector is capable of connecting with a front end of a circuit in a container of dialysis solution, and a channel for solution is connected by fitting the outer cylinder of the circuit side connector with the patient side connector,
   when the protective cap is fitted with the patient side connector, the inner cap assumes a state of being retained at the front end side of the patient side connector,
   when the protective cap is removed from the patient side connector, the inner cap is detached from the protective cap because of a retaining force at the front end side of the patient side connector,
   when the patient side connector with the inner cap retained at the front end thereof is connected with the circuit side connector, the internal end portion of the inner cylinder penetrates through the disinfectant-impregnated member in the inner cap, so that the channel is opened, and
   when the connection between the patient side connector and the circuit side connector is released, the inner cap is retained inside the circuit side connector and is detached from the front end of the patient side connector.

2. The connector system for sterile connection according to claim 1,
   wherein the patient side connector comprises a septum member at a front end portion thereof for protecting the channel, and
   when the patient side connector with the inner cap retained at the front end thereof is connected with the circuit side connector, the internal end portion of the inner cylinder penetrates through the disinfectant-impregnated member in the inner cap and the septum member of the patient side connector, so that the channel is opened.

3. The connector system for sterile connection according to claim 1,
   wherein the inner cap comprises a plurality of engaging legs extending from an outer edge portion of the ring-shaped portion in a direction along an axis of the ring, an engaging convexity is formed at a front end of each of the engaging legs so as to protrude inward, engaging concavities are formed on an outer surface of the front end portion of the patient side connector so as to allow engagement with the engaging convexities formed at the engaging legs of the inner cap, an inner cap retaining portion is formed on an inner wall inside the protective cap, where a retaining force exerted by the engagement between the engaging convexity of the inner cap and the engaging concavity of the patient side connector is larger than a force exerted by the inner cap retaining portion of the protective cap to retain the inner cap,
   when the protective cap with the inner cap retained therein is fitted with the patient side connector, the engaging convexities of the inner cap engage with the engaging concavities of the patient side connector, and
   when the protective cap is removed from the patient side connector, the retaining of the inner cap by the inner cap retaining portion of the protective cap is released due to the retaining of the inner cap at the engaging concavities of the patient side connector, so that the inner cap is detached from the protective cap while being fitted with the front end of the patient side connector.

4. The connector system for sterile connection according to claim 3, wherein on the outer surface of the patient side connector, a circumferential step portion extending in a circumferential direction is formed so that a diameter at the front end side of the patient side connector is smaller than that at a base end side, and a guide groove is formed so as to extend from the circumferential step portion toward the base end, the guide groove including an inclined portion that is inclined with respect to an axis of the patient side connector, on the inner wall close to an opening end portion of the protective cap, a guide protrusion is formed, and on the inner wall and extending toward the closed end side of the protective cap, a rotation blocking step portion is formed, the rotation blocking step portion being capable of contacting with the engaging legs of the inner cap so as to block a rotational action of the inner cap, when the patient side connector is inserted into an opening of the protective cap with the guide protrusion of the protective cap facing the guide groove of the patient side connector, and then the protective cap and the patient side connector are rotated while being urged axially toward each other, the guide protrusion slides along the guide groove, so that the patient side connector is pulled into an inside of the protective cap by a driving force resulting from a screw action by the inclined portion of the guide groove, and the engaging convexities of the inner cap, whose rotation is blocked by the rotation blocking step portion, engage with the engaging concavities of the patient side connector.

5. The connector system for sterile connection according to claim 4, wherein the patient side connector comprises a blocking wall at the front end portion thereof, which is capable of contacting with a side face portion of the engaging leg of the inner cap when the inner cap is fitted thereto, and the outer cylinder of the circuit side connector comprises: a guide protrusion formed on an inner wall close to an open end portion thereof, the guide protrusion being formed to correspond to the guide protrusion of the protective cap; a guide step portion including an inclined portion that is inclined with respect to an axis of the circuit side connector; and an inner cap retaining portion formed at an inside of the connector and being capable of retaining the inner cap, when the patient side connector with the inner cap retained therein is inserted into the opening of the circuit side connector with the guide protrusion of the outer cylinder facing the guide groove of the patient side connector, and then the circuit side connector and the patient side connector are rotated while being urged axially toward each other, the guide protrusion slides along the guide groove, so that the patient side connector is pulled into the inside of the circuit side connector by a driving force resulting from a screw action by the inclined portion of the guide groove, and at the same time the front ends of the engaging legs of the inner cap slide along the inclined portion of the guide step portion of the circuit side connector while rotation of the inner cap is blocked by the blocking wall of the patient side connector, so that a force in the axis direction acts on the inner cap so as to separate the inner cap from the patient side connector, resulting in release of the engagement between the inner cap and the patient side connector, and the inner cap assumes a state of being retained by the inner cap retaining portion of the outer cylinder.

6. The connector system for sterile connection according to claim 5, wherein the inner cap retaining portion of the circuit side connector is configured with a horizontal step portion provided at the innermost of the guide step portion, and when the front ends of the engaging legs of the inner cap contact with the horizontal step portion, the inner cap is prevented from moving in the axis direction toward the opening of the outer cylinder so as to be retained in the circuit side connector.

7. The connector system for sterile connection according to claim 5, wherein the inner cap retaining portion of the circuit side connector is configured by setting dimensions of constituting elements so that at least portions of the inner wall of the inside of the outer cylinder contact with an outer circumferential surface of the ring-shaped portion of the inner cap or so that at least portions of the outer wall of the internal end portion of the inner cylinder contact with an inner circumferential surface of the ring-shaped portion of the inner cap, whereby the inner cap is retained by the thus generated frictional force.

8. The connector system for sterile connection according to claim 3, wherein the inner cap retaining portion of the protective cap is configured with a convex stripe formed on the inner wall of the inside of the protective cap, and the convex stripe contacts with an outer circumferential surface of the ring-shaped portion of the inner cap, so that the inner cap is retained by the thus generated frictional force.

9. The connector system for sterile connection according to claim 4, wherein on the outer surface of the front end portion of the patient side connector, a convex stripe is formed so as to extend in the axis direction to a portion close to a joining portion between the guide groove and the circumferential direction step portion, and when the protective cap or the circuit side connector is combined with the patient side connector, the convex stripe guides the guide protrusion of each of the protective cap and the circuit side connector to the guide groove.

10. The circuit side connector used in the connector system for sterile connection according to claim 1, comprising a double-cylinder structure in which an inner cylinder is fixed at one end portion of an outer cylinder, the inner cylinder including an internal end portion located inside the outer cylinder and an external end portion exposed outside the outer cylinder.

11. The protective cap assembled member used in the connector system for sterile connection according to claim 3, comprising:

the protective cap having a substantially cylindrical shape whose one end is closed; and the inner cap retained at an inside of the protective cap and including a ring-shaped portion with a disinfectant-impregnated member supported therein, wherein on an inner wall of the inside of the protective cap, an inner cap retaining portion for retaining the inner cap is formed, the inner cap includes a plurality of engaging legs extending from an outer edge portion of the ring-shaped portion in a direction along an axis of the ring, and an engaging convexity is formed at each of the engaging legs so as to protrude inward, and the inner cap is retained in the inner cap retaining portion so that the front ends of the engaging legs are directed toward an opening of the protective cap.

12. The patient side connector used in the connector system for sterile connection according to claim 3, comprising engaging concavities formed on an outer surface of the front end portion thereof so as to allow engagement with the engaging convexities formed at the engaging legs of the inner cap.

* * * * *